United States Patent [19]

Rademacher et al.

[11] Patent Number: 5,100,778
[45] Date of Patent: Mar. 31, 1992

[54] OLIGOSACCHARIDE SEQUENCING

[75] Inventors: Thomas W. Rademacher; Mark R. Wormald; Raj B. Parekh; Christopher J. Edge; Raymond A. Dwek, all of Oxford, United Kingdom

[73] Assignee: Monsanto Company, St. Louis, Mo.

[21] Appl. No.: 416,633

[22] Filed: Oct. 3, 1989

[51] Int. Cl.$^5$ .............................................. C12Q 1/25
[52] U.S. Cl. ........................................ 435/18; 435/22; 435/101
[58] Field of Search .......................... 435/18, 22, 101

[56] References Cited

U.S. PATENT DOCUMENTS 4,659,659 4/1987 Dwek et al. .......................... 435/18
4,751,084 6/1988 Feder et al. ...................... 424/94.64

OTHER PUBLICATIONS

Harada, Anal-Biochem. 164,374-381 (1987).
Parekh et al., Nature 316,452-457 (1985).
Kobata, Anal. Biochem. 100,1-14 (1979).

Primary Examiner—Robert A. Wax
Assistant Examiner—Jeffrey Stucker
Attorney, Agent, or Firm—Scott J. Meyer; James W. Williams, Jr.

[57] ABSTRACT

A method of oligosaccharide sequencing in which the components are determined essentially simultaneously is disclosed which comprises a series of steps as follows:

A. Placing an identifying label on the reducing terminal residue of the oligosaccharide to be sequenced, B. Dividing said oligosaccharide into a plurality of separate portions of known integer amounts, C. Treating each said portion with a different reagent mix to thereby provide a series of reaction mixtures, D. Pooling known integer amounts of the products from each separate reaction mixture to give a product pool, E. Performing an analysis on said product pool which measures the molar proportions of the reaction products, and F. Reconstructing or identifying the starting oligosaccharide from the molar prevalence of said reaction products.

10 Claims, 19 Drawing Sheets

|         | 1 | 2 | 3 | 3' | 4 | 4' | 5 | 5' | 6 | 6' |
|---------|---|---|---|----|---|----|---|----|---|----|
| ENZYME a  | ○ | ○ | * | *  | * | *  | * | *  | * | *  |
| ENZYME a' | ○ | ○ | * | ○  | * | ○  | * | ○  | * | ○  |
| ENZYME b  | ○ | * | ○ | ○  | * | *  | * | *  | * | ○  |
| ENZYME c  | ○ | * | * | *  | ○ | ○  | * | *  | * | *  |
| ENZYME d  | ○ | * | * | *  | * | *  | ○ | ○  | * | *  |

ENZYME MIXES

FIG. 2C

| DIGEST MIX | RESULT | FINAL FRAGMENT PROFILE | |
|---|---|---|---|
| | | POSITION | INTENSITY |
| $U_1$ | PEAK AT 2.5 g.u. | 13.5 | 2 |
| $U_2$ | PEAK AT 13.5 g.u. | 11.5 | 1 |
| $U_3$ | PEAK AT 11.5 g.u. | 7.5 | 1 |
| $U_4$ | PEAK AT 7.5 g.u. | 5.5 | 1 |
| $U_5$ | PEAK AT 5.5 g.u. | 2.5 | 1 |
| $U_6$ | PEAK AT 13.5 g.u. | | |

A. JACK BEAN β-GALACTOSIDASE
B. JACK BEAN β-N-ACETYLHEXOSAMINIDASE
C. JACK BEAN β α-MANNOSIDASE
D. ACHATINA FULICA β-MANNOSIDASE

+ THE DOTTED LINES SHOW THE RESIDUES OF CLEAVED IF THEY ARE PRESENT ON A NON-REDUCING TERMINI.

\* THE NUMBER 0 INDICATES THE HYDRODYNAMIC VOLUME CONTRIBUTION OF EACH MONOSACCHARIDE RESPECTIVELY.

FIG. 4B

|  | ENZYME ARRAY | ENZYME MIXES | | | | | | |
|---|---|---|---|---|---|---|---|---|
| ENZYMES | 1 | 2 | 3 | 4 | 5 | 6 | 7 |
| JACK BEAN β-GALACTOSIDASE | O | O | * | * | * | * | * |
| JACK BEAN β-HEXOSAMINIDASE | O | * | O | * | * | * | * |
| STREPTOCOCCUS β-HEXOSAMINIDASE | O | * | * | O | * | * | * |
| JACK BEAN α-MANNOSIDASE | O | * | * | * | O | * | * |
| SNAIL β-MANNOSIDASE | O | * | * | * | * | O | * |

FIG. 6

| ENZYMES | ENZYME ARRAY | ENZYME MIXES | | | | | | |
|---|---|---|---|---|---|---|---|---|
| | | 1 | 2 | 3 | 4 | 5 | 6 | 7 |
| BOVINE EPIDIDYMAL α-FUCOSIDASE | | O | O | * | * | * | * | * |
| JACK BEAN β-GALACTOSIDASE | | O | * | O | * | * | * | * |
| JACK BEAN β-HEXOSAMINIDASE | | O | * | * | O | * | * | * |
| JACK BEAN α-MANNOSIDASE (ARM SPECIFIC) | | O | * | * | * | O | * | * |
| ACHITINA FULICA β-MANNOSIDASE | | O | * | * | * | * | O | * |

FIG. 11A

EXPANDED BLANKED DIAGONAL ARRAY

ENZYME MIXES

| | 1 | 2 | 3 | 4 | 5 | 6 | 6' | |
|---|---|---|---|---|---|---|---|---|
| | O | O | * | * | * | * | O | JACK BEAN α-MANNOSIDASE |
| | O | O | * | * | * | * | * | ALMOND β-XYLOSIDASE |
| | O | * | O | * | * | * | * | ACHITINA FULICA β-MANNOSIDASE |
| | O | * | * | O | * | * | * | JACK BEAN β-HEXOSAMINIDASE |
| | O | * | * | * | O | * | * | ALMOND α-FUCOSIDASE I |

BLANKED DIAGONAL ARRAY

ENZYME MIXES

| | 1 | 2 | 3 | 4 | 5 | 6 |
|---|---|---|---|---|---|---|
| | O | O | * | * | * | * |
| | O | O | * | * | * | * |
| | O | * | O | * | * | * |
| | O | * | * | O | * | * |
| | O | * | * | * | O | * |

FIG. 13A

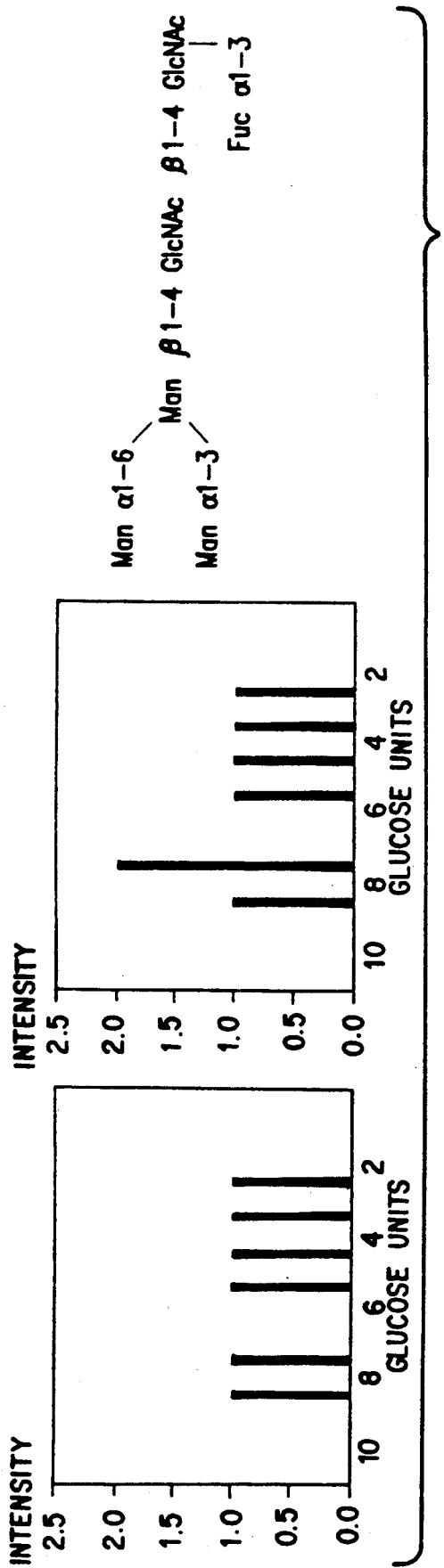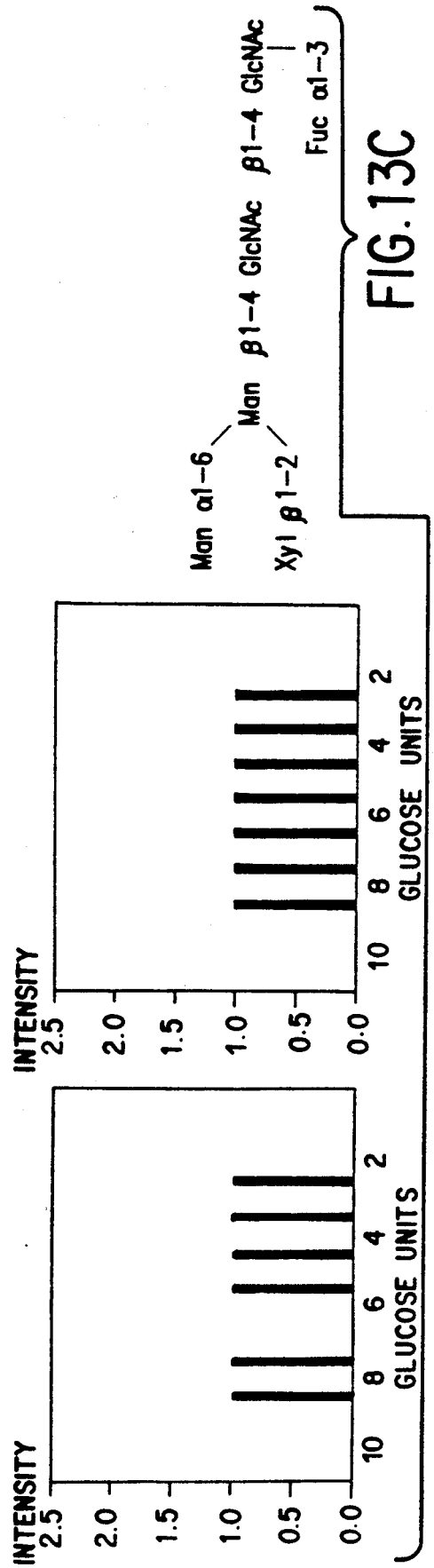
FIG. 13B
FIG. 13C

OLIGOSACCHARIDE SEQUENCING

BACKGROUND OF THE INVENTION

This invention relates to a method of sequencing oligosaccharides and, more particularly, to a method of oligosaccharide sequencing in which the components are determined essentially simultaneously.

Numerous analytical techniques for sequencing compounds are available which rely upon the use of well defined chemical or enzymatic reactions followed by the analysis of their products to identify the starting compound. For example, protein sequencing such as the Edman degradation has been widely used for many years for the direct determination of the primary structure of proteins and peptides [Edman, *Acta Chem. Scand.* 10, 761 (1956); Hunkapiller and Hood, *Science* 219, 650–659 (1983)]. The more recent introduction of rapid, simple methods of DNA sequencing also has become an important tool for biochemistry and molecular biology. The most widely used such DNA sequencing techniques are that of Maxam and Gilbert, *Proc. Natl. Acad. Sci. USA* 74, 560–564 (1977), and Sanger et al., *Proc. Natl. Acad. Sci. USA* 74, 5463–5467 (1977).

Methods have also been developed for determining the sequence of oligosaccharides such as that described by Kobata in "The Carbohydrates of Glycoproteins, Biology of Carbohydrates," (Ginsburg and Robins, Eds.), John Wiley and Sons, Vol. 2, pp. 87–162, 1984; Snider, *Ibid.*, pp. 163–193, 1984. See also Harada et al., *Anal. Biochem.* 164, 374–381 (1987). Most proteins are glycoproteins which contain either O-glycosidically linked or N-glycosidically linked saccharides. These saccharides may vary from a single monosaccharide to highly branched structures containing over 30 monosaccharide residues. The determination of a monosaccharide sequence in such an oligosaccharide involves determining the order and branching pattern of the monosaccharide residues, the orientation of each glycosidic linkage ($\alpha$ or $\beta$) and the linkage between the various monosaccharides, i.e. 1→3, 1→4, etc.

Most of the available analytical techniques for sequencing are sequential in nature, that is, a single reaction is performed and its products are analyzed, followed by a second reaction and a second analysis, performed either on the starting material or on the products of the first reaction. The sequential nature of these techniques can be illustrated by the following schematic outline:

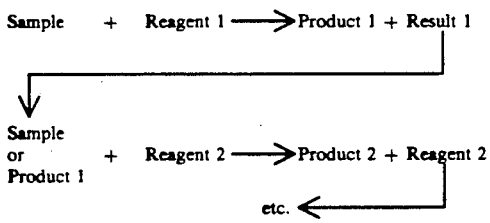

These sequential techniques have the advantage of great flexibility and sensitivity. That is, each subsequent reaction can be selected on the basis of the previous results (flexibility), and the products of one reaction can be used as the starting point for the next (sensitivity). However, there also are disadvantages in these techniques in that the process can be slow, being a sequential technique, and difficult to automate unless the procedure is predefined, thereby resulting in loss of its flexibility.

Determination of the sequence and structure of oligosaccharides can be of significant importance in various fields, particularly in the medical and pharmaceutical fields. For example, the carbohydrate structure of a glycoprotein can have a significant effect upon its biological activity. That is, the oligosaccharides can affect the protein's antigenicity, stability, solubility and tertiary structure. The carbohydrate side-chains also can influence the protein's half-life and target it to receptors on the appropriate cells. The carbohydrate residues can affect both inter- and intracellular recognition. The sugar groups thus can control the relative effectiveness of a therapeutic protein when administered to a patient. These and other such functions of the carbohydrate moiety of glycoproteins are discussed, for example, by Delente, *Trends in Biotech.* 3(9), 218 (1985); van Brunt, *Bio/Technology* 4, 835–839 (1986); and Taunton-Rigby, *Biotech USA* 1988, Proc. Conf. San Francisco, Nov. 14–16, 1988, pp. 168–176.

It is also apparent that differences in the glycosylation pattern (i.e., particular structure at a specific site) on similar proteins or proteins with identical amino acid sequences can have profound effects on antigenicity, metabolism and other physiological properties. See, for example, the report on "The association of rheumatoid arthritis and osteoarthritis with changes in the glycosylation pattern of total serum" by Parekh et al., *Nature* 316, 452–457 (1985) and in U.S. Pat. No. 4,659,659.

The practical use of oligosaccharide sequencing also is illustrated with the medically important anti-thrombolytic glycoprotein known as tissue plasminogen activator (tPA) in U.S. Pat. No. 4,751,084. Improved methods of carrying out such oligosaccharide sequencing thus would have significant value in the medical and pharmaceutical fields and elsewhere.

BRIEF DESCRIPTION OF THE INVENTION

In accordance with the present invention a novel method of oligosaccharide sequencing is provided in which the components are determined essentially simultaneously. For convenience, this method also is designated herein as the Reagent Array Analysis Method (RAAM).

In the prior art sequential method of oligosaccharide sequencing, the presence of specific linkages is determined by the ability of a given enzyme to cause cleavage. In the RAAM method, the presence of a given linkage is determined by the inability of a reagent mix lacking a given cleavage reagent, e.g. a particular enzyme, to cleave that linkage. As all other linkages can be cleaved until that given linkage is reached, that linkage forms a stop point for cleavage by that reagent mix. The position of the stop point in the oligosaccharide is then determined by the size of the remaining fragment. If that linkage does not occur, no stop point is reached and full cleavage takes place.

The method of the invention is conveniently described as comprising a series of steps as follows:

A. Placing an identifying label on the reducing terminal residue of the oligosaccharide to be sequenced, B. Dividing said oligosaccharide into a plurality of separate portions of known integer amounts, C. Treating each said portion with a different reagent mix to thereby provide a series of reaction mixtures, D. Pooling known integer amounts of the products from each separate reaction mixture to give a product pool, E. Performing an analysis on said product pool which measures the molar proportions of the reaction products, and F. Reconstructing or identifying the starting oligosaccharide from the molar prevalence of said reaction products.

The simultaneous nature of the method of the invention can be illustrated by the following schematic outline:

```
Reagent Array              Analysis reagent mix 1
   /
  / reagent mix 2  \
 /                  \
Sample          Product pool ——> Spectrum
 \                  /
  \                /
    reagent mix n
```

Two principal advantages of the method of the invention are that it is well defined and thus suitable for automation and that it is much faster than sequential techniques, all reactions being carried out simultaneously and a simple analysis being performed at the end.

DETAILED DESCRIPTION OF THE INVENTION

While the specification concludes with claims particularly pointing out and distinctly claiming the subject matter regarded as forming the present invention, it is believed that the invention will be better understood from the following description of preferred embodiments of the invention taken in conjunction with the accompanying drawings in which:

Figures 1A, 1B:
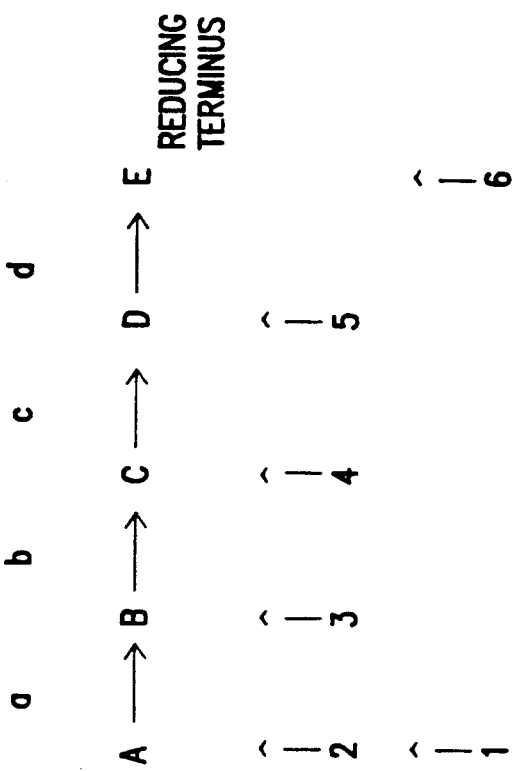
FIG. 1A is a schematic of one embodiment of the invention in which a linear oligosaccharide represented as A → B → C → D → E is cleaved at its disaccharide linkages with exoglycosidases a, b, c and d with enzyme reaction stop points 1, 2, 3, 4, 5 and 6 generated by the enzyme mixes shown in FIG. 1B. Presence of enzymes=*; absence of enzymes=0.
Figures 2A, 2B:
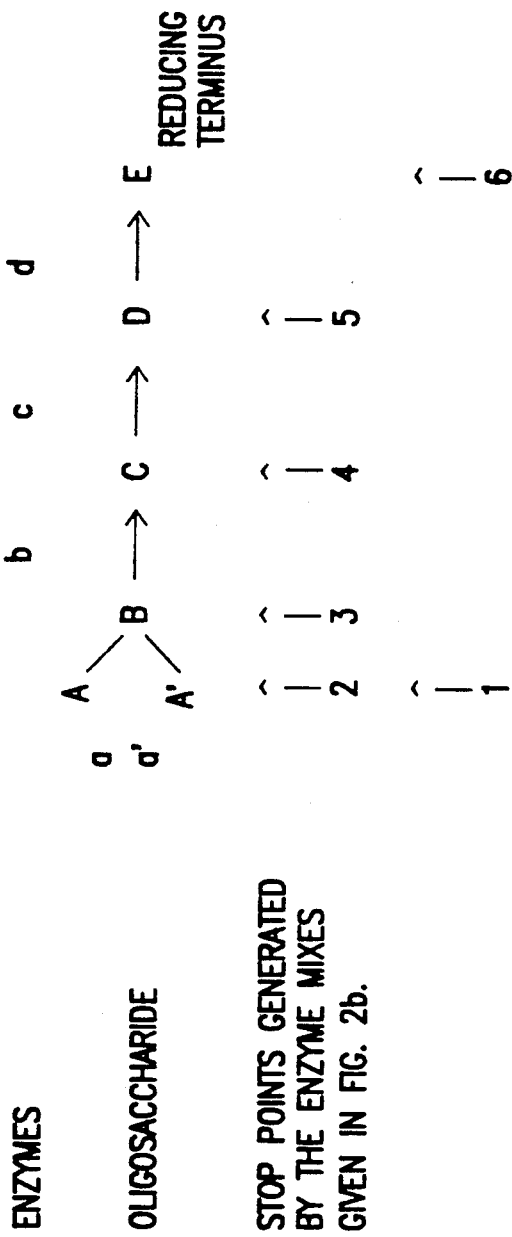
FIG. 2A is a schematic of another embodiment of the invention in which branched oligosaccharide

```
   A
    \
     B ——>C ——>D ——>E
    /
   A'
``` is treated as the oligosaccharide in FIG. 1 but in which a mix of enzymes a + a' is used instead of enzyme a (FIG. 2B) or is treated with an expanded group of enzyme mixes (FIG. 2C).

Figure 3:
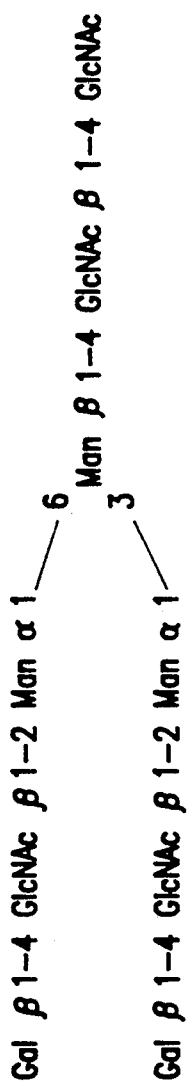
Figure 3:
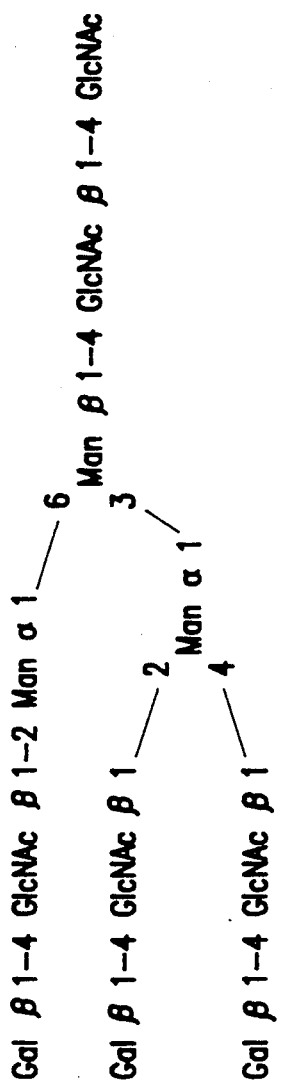
Figure 3:
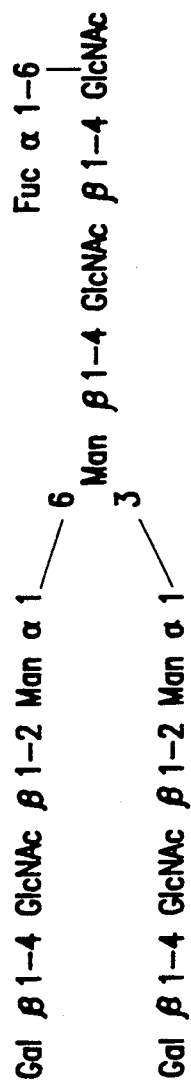

FIG. 3 shows the structures of three illustrative complex oligosaccharides sequenced in accordance with other embodiments of the invention. Structure I=a complex biantennary oligosaccharide; Structure II=a complex triantennary oligosaccharide; Structure III=a complex fucosylated biantennary oligosaccharide.

Figure 4A:
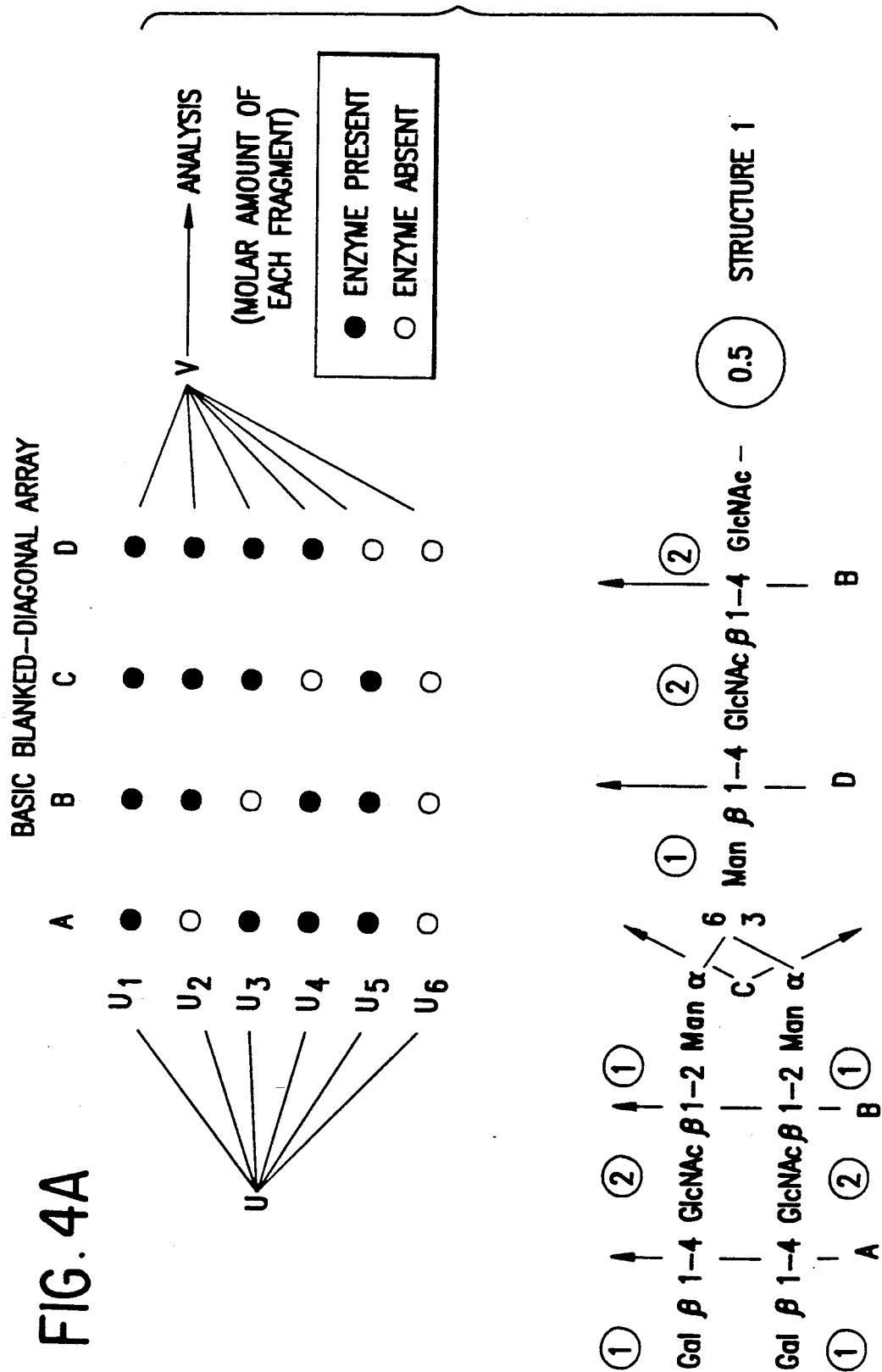

FIGS. 4A-4B are a schematic which shows the Reagent Array Analysis Method (RAAM) for the sequencing of the oligosaccharide Structure I of FIG. 3.

Figure 5:
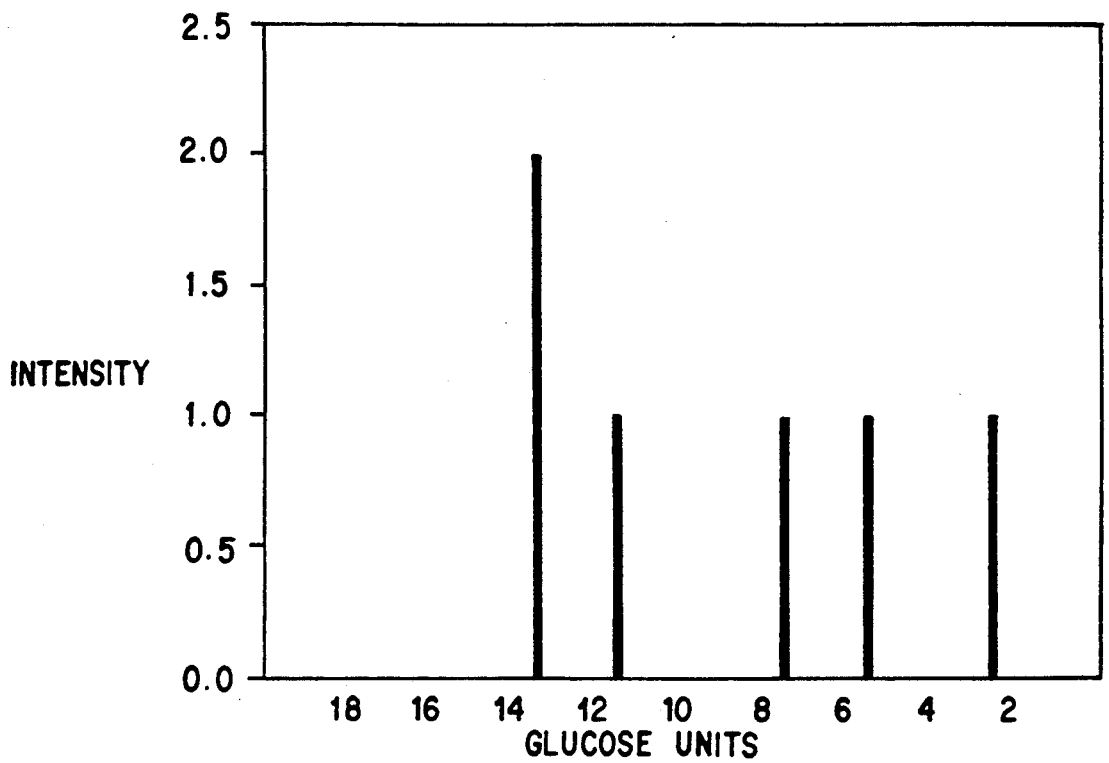

FIG. 5 is a graphical representation which shows the computer simulated Bio-Gel P-4 RAAM profile (intensity vs. glucose units) for the oligosaccharide sequenced in FIG. 4.

Figure 8:
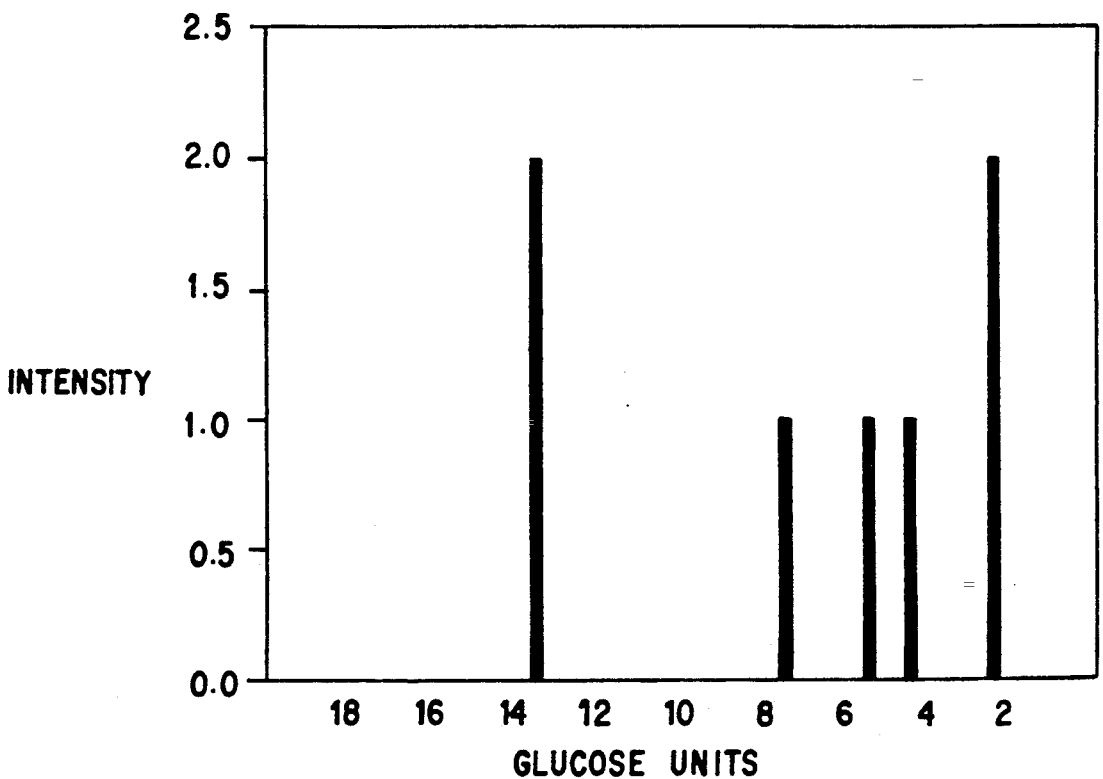
Figure 10:
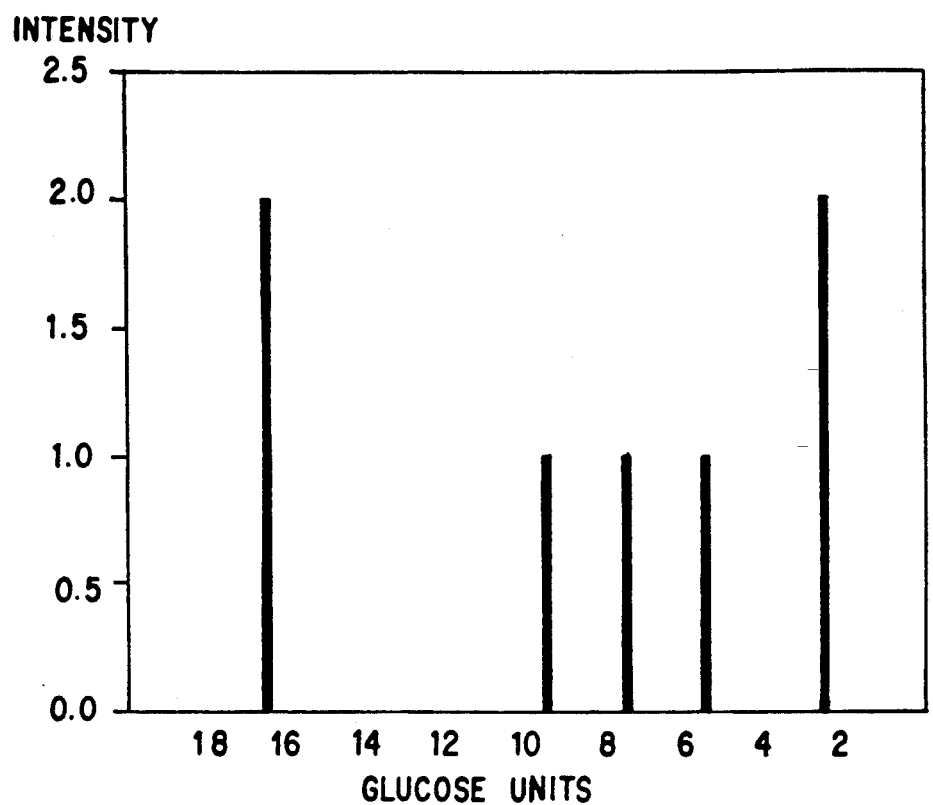

FIG. 6 shows an enzyme array used for the sequencing of the oligosaccharides in other embodiments of the invention in FIGS. 8, 10 and 12.

Figure 7:
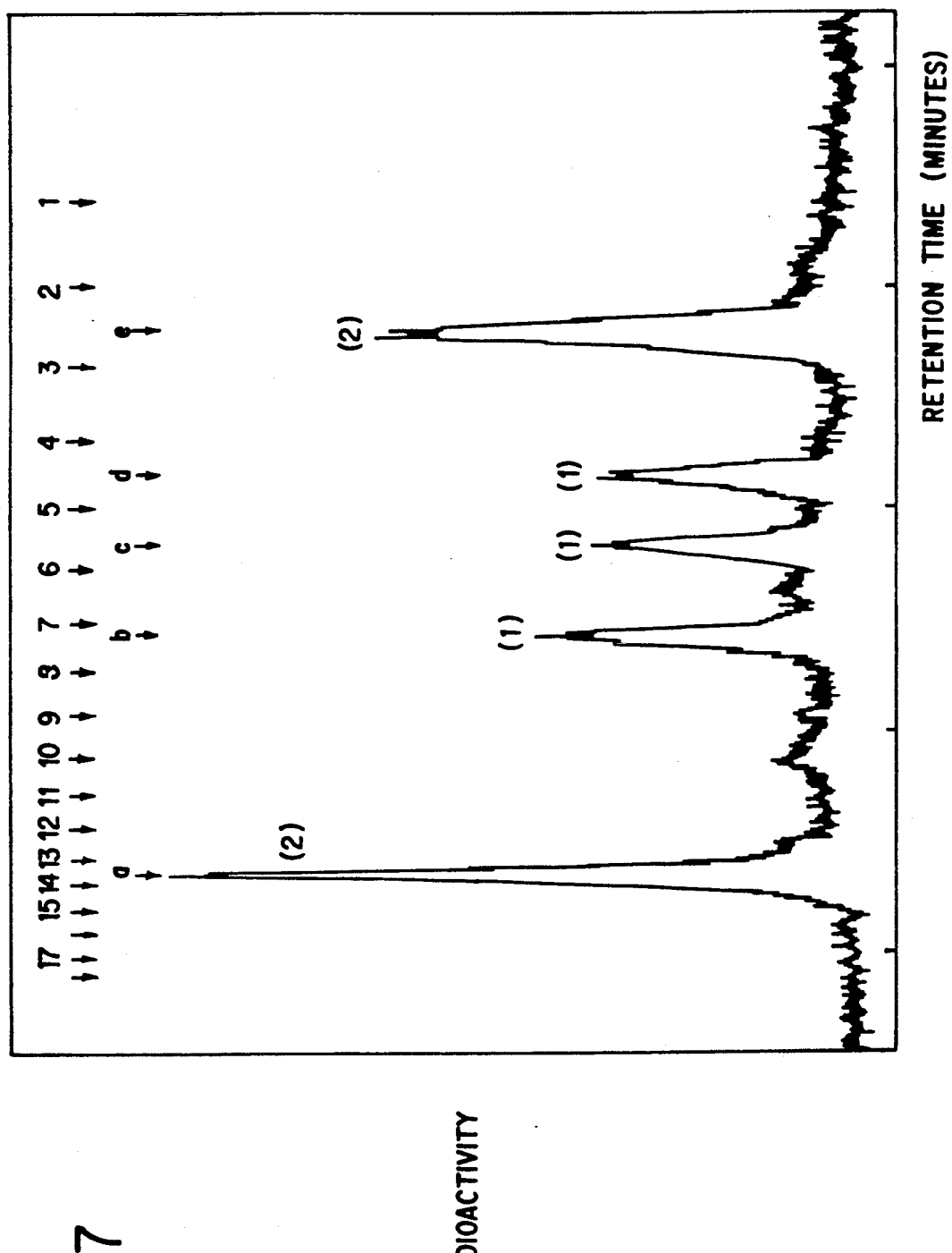

FIG. 7 shows the Bio-Gel P-4 chromatogram in which the intensities (counts/min) of the fractions are plotted against the hydrodynamic volume (in glucose units) of an internal standard acid hydrolysate of dextran.

FIG. 8 shows the computer simulate Bio-Gel P-4 RAAM profile for the oligosaccharide sequenced in FIG. 7 with the enzyme array shown in FIG. 6.

Figure 9:
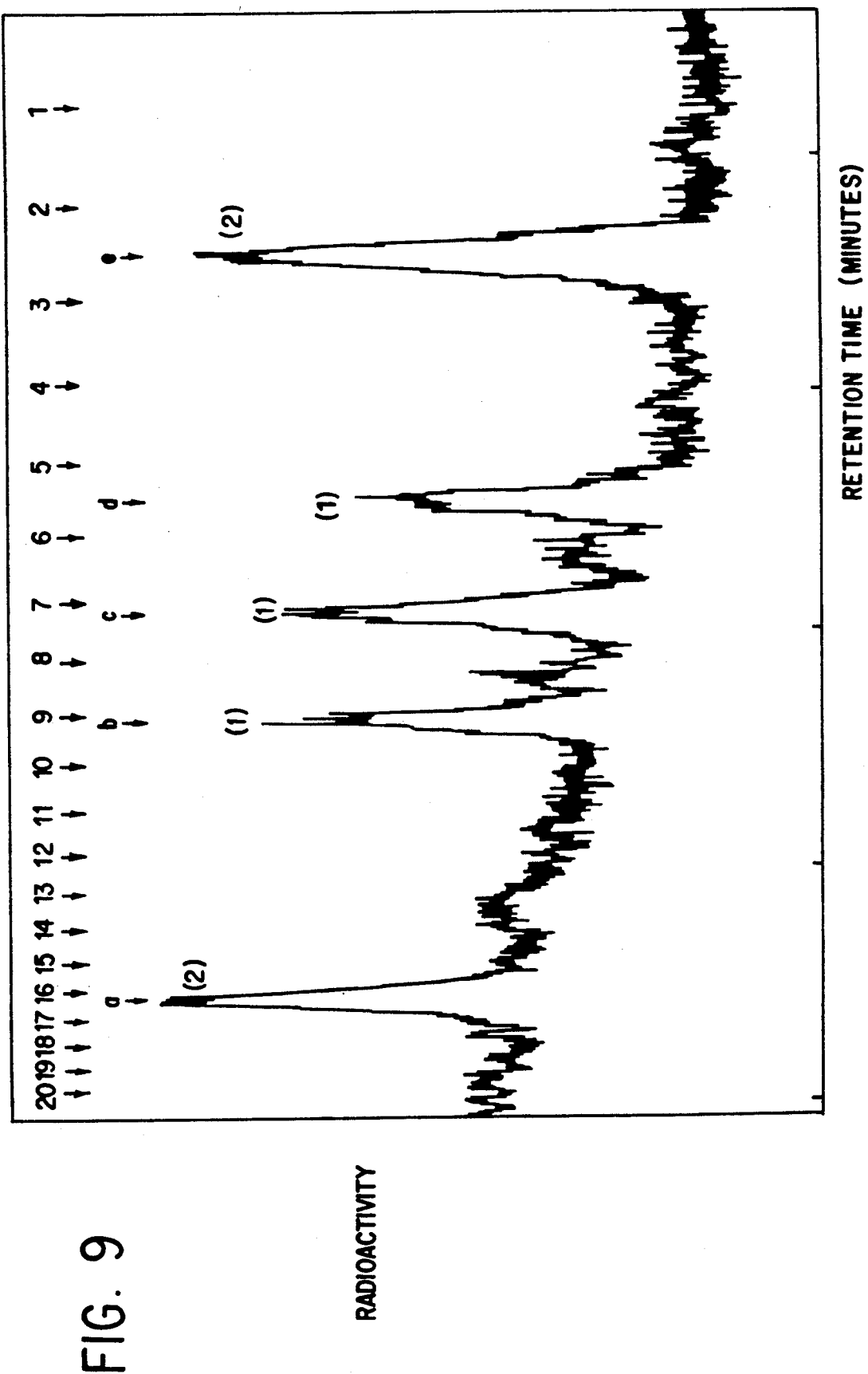

FIG. 9 shows in another embodiment of the invention the Bio-Gel P-4 chromatogram in which the intensities (counts/min) of the fractions are plotted against the hydrodynamic volume (in glucose units) of an internal standard acid hydrolysate of dextran.

FIG. 10 shows the computer simulated Bio-Gel P-4 RAAM profile for the oligosaccharide sequenced in FIG. 9 with the enzyme array shown in FIG. 6.

Figure 11B:
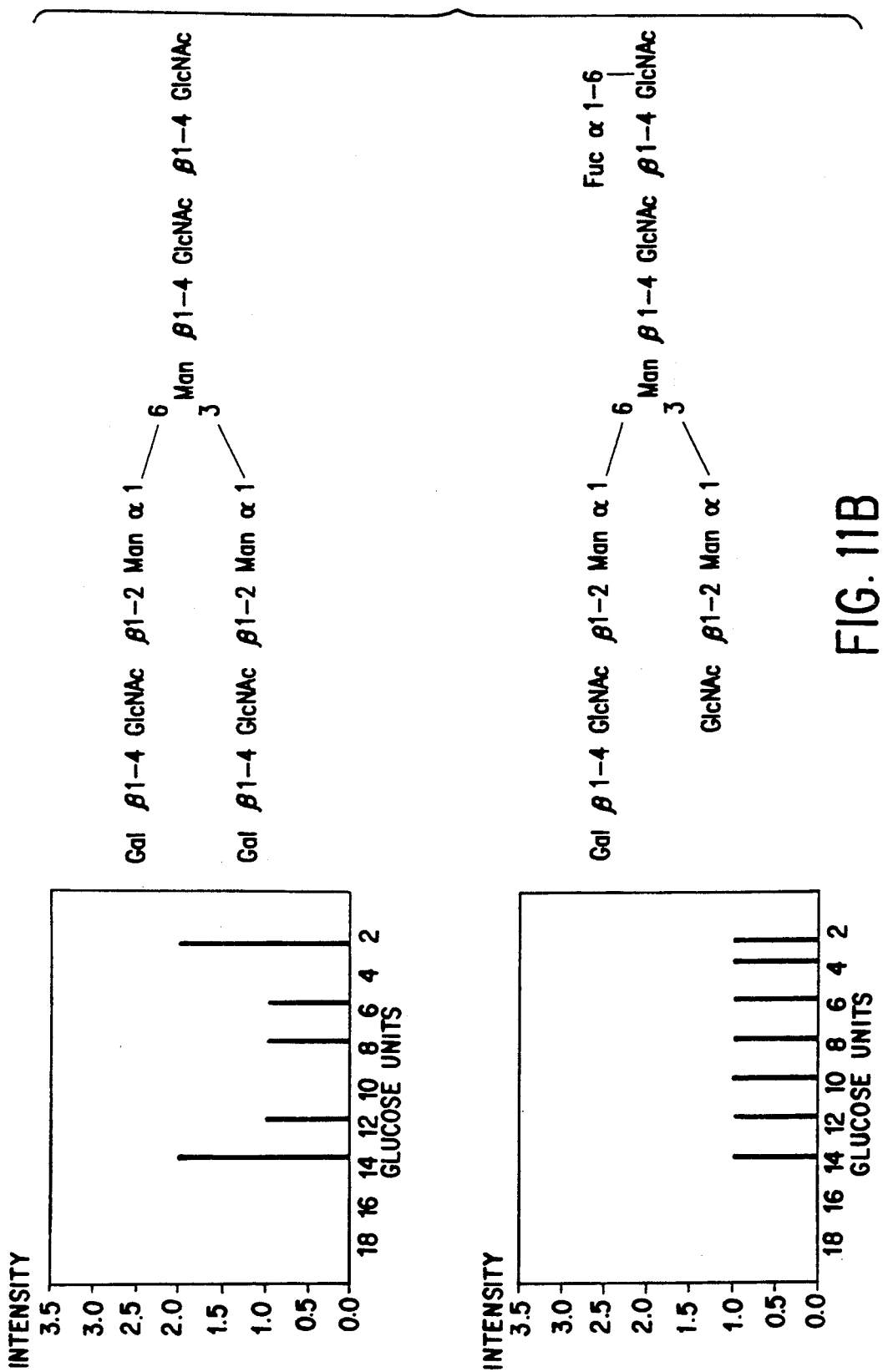
Figure 11C:
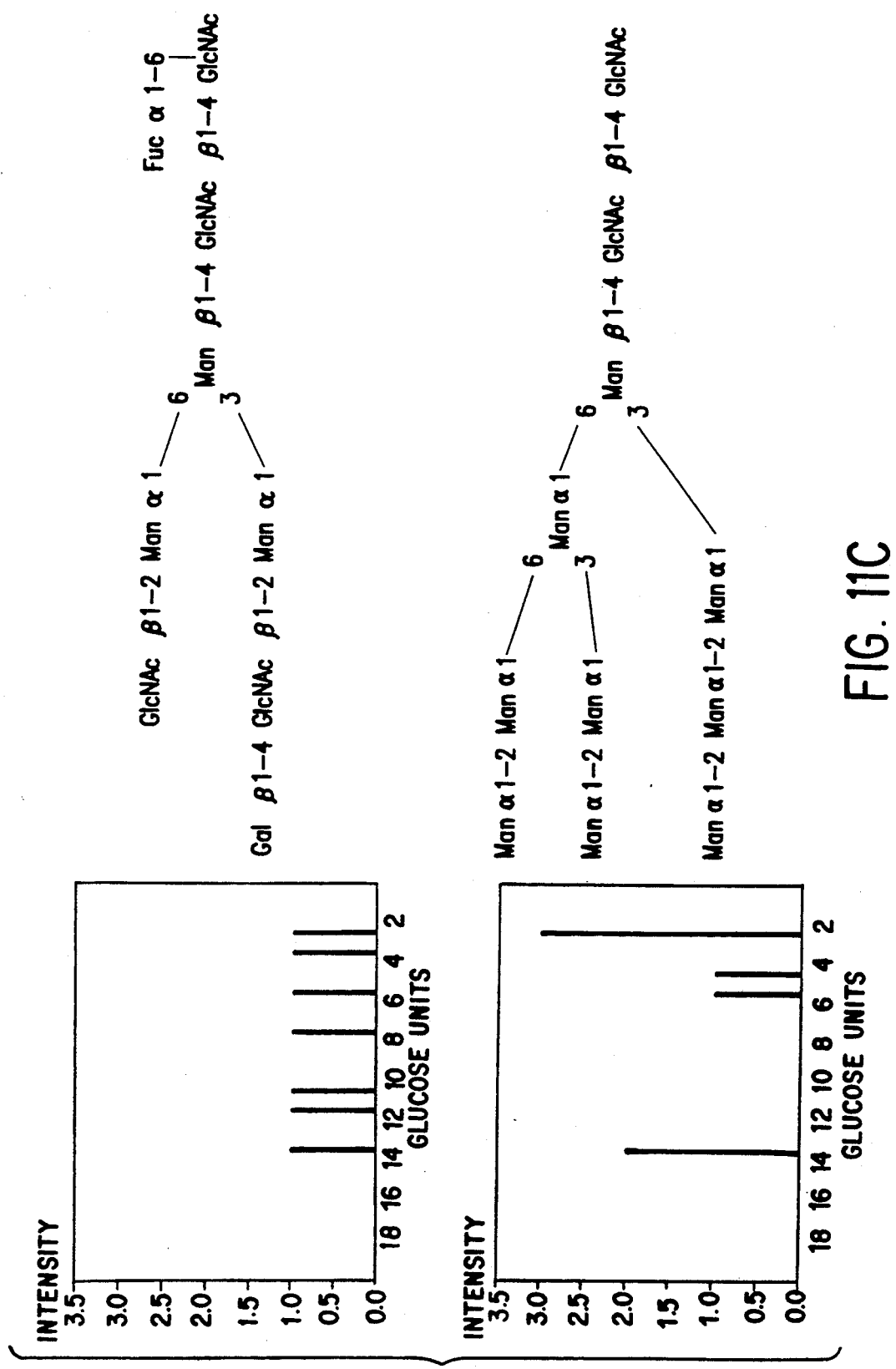

FIGS. 11A-11C show the computer simulated P-4 RAAM profiles for the oligosaccharides depicted using the enzyme array also shown in the figure.

Figure 12A:
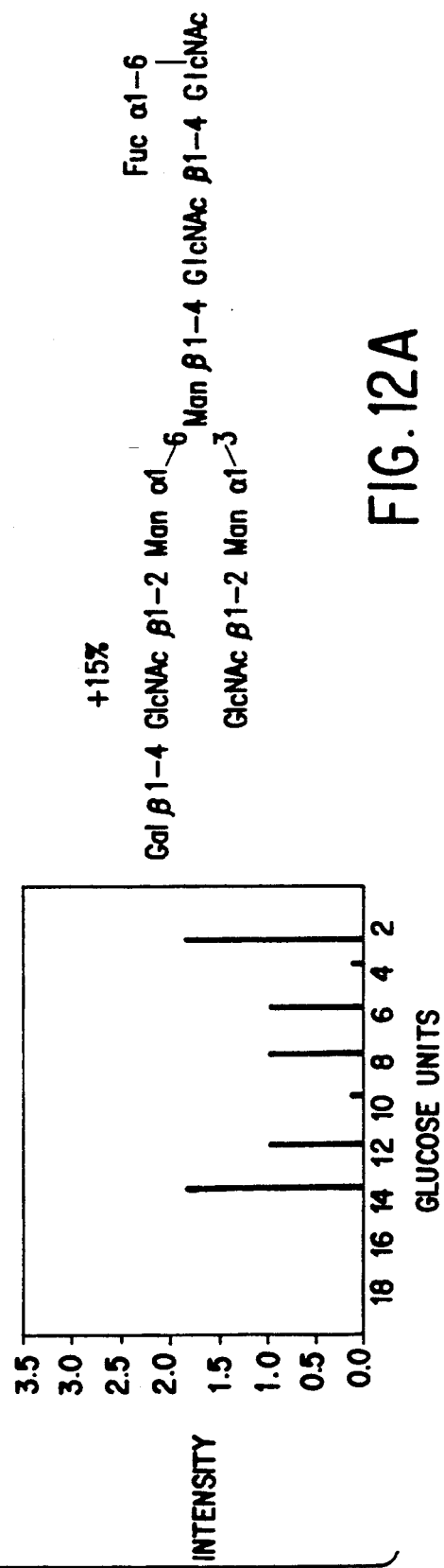
Figure 12B:
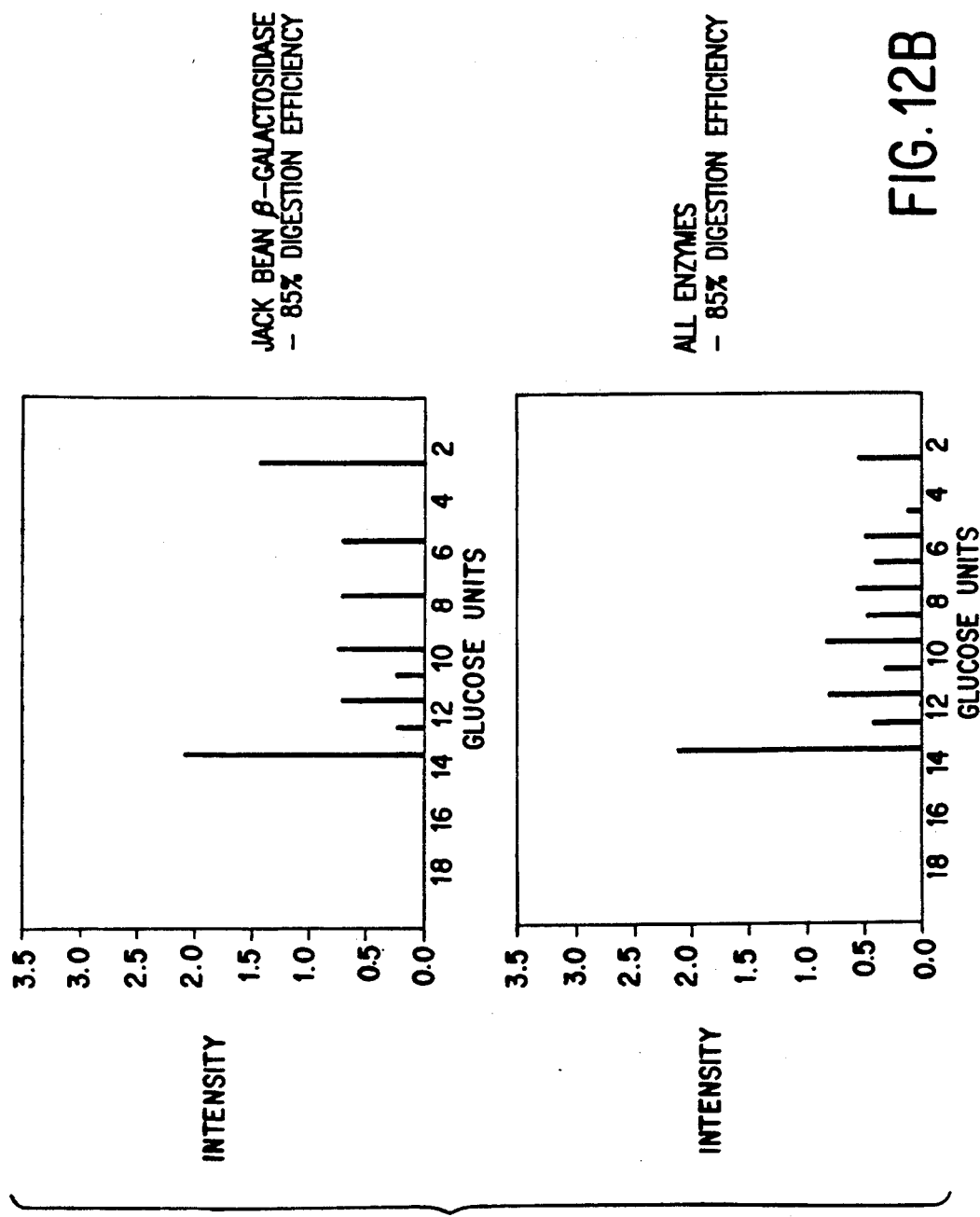

FIGS. 12A-12B show the computer simulated P-4 RAAM profiles for the oligosaccharide shown using the enzyme array also depicted in the figure. The top RAAM profile show the effect of a 15% contaminant of a monogalactosylated fucosylated biantennary oligosaccharide (compare to top RAAM profile of FIG. 11. Also shown are the effects of incomplete enzymatic digestions.

FIGS. 13A-13C show how an expanded blanked diagonal array can be used to discriminate between two similar oligosaccharides which give the same RAAM profile using a blanked diagonal array.

Figure 14B:
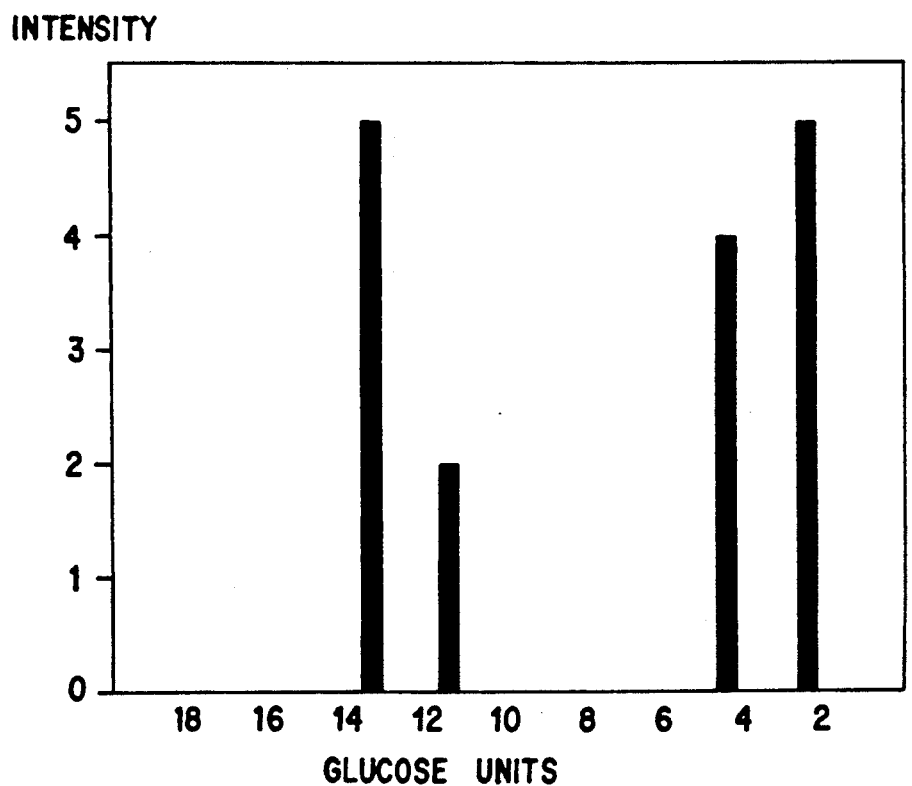
Figure 14A:
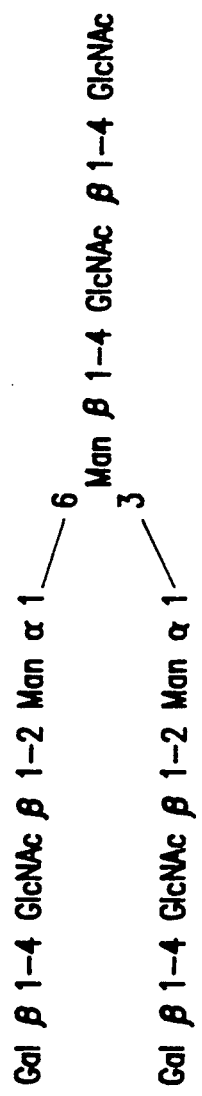

FIGS. 14A-14B show an expanded enzyme array and the resulting RAAM profile on the oligosaccharide depicted in the figure.

The oligosaccharides which can be sequenced in accordance with the method of the invention can be obtained from a variety of plant and animal sources, for example:

(1) Purified glycoproteins and glycohormones;
(2) Whole serum and its fractions;
(3) Biological secretions such as, for example, urine, milk, meconium, mucus, colostrum and the like substances;
(4) Whole organs, for example, kidneys, liver, heart, spleen, pancreas, lung;
(5) Plant stem and leaf extracts;
(6) Seed material;
(7) Lectins; and
(8) Emulsins.

Release of oligosaccharides containing reducing terminal residues from such plant and animal material by chemical means such as hydrazinolysis is described in U.S. Pat. Nos. 4,719,294 and 4,736,022 and by Takasaki et al., Meth. Enzymol. 83, 263-268 (1982).

Release of oligosaccharides containing reducing terminal residues by enzymatic methods is illustrated by the use of N-glycanase as described by Hirani et al., *Anal. Biochem.* 162, 485-492 (1987).

The identifying label to be placed on the reducing terminal residue of the oligosaccharide to be sequenced can be, for example, a radioactive label, a spectroscopically active reporter group or a chemically active reporter group. Illustrative of such labels are radioactive $^3$H, a 2-amino-pyridine label and a glycosylamine-attached fluorescent label. A radioactive label on the oligosaccharide can be provided, for example, by reduction of the reducing terminal N-acetylglucosamine residues with NaB$^3$H$_4$.

The oligosaccharide sample thus labeled is divided into a predetermined number of separate portions which must be of known integer amounts. In an illustrative embodiment of the invention the oligosaccharide is divided into a plurality of equal portions which are two in number more than the number of disaccharide linkages to be determined. However, the number of sample portions need not be related to the number of oligosaccharide linkages.

The reagents used for treating the separate oligosaccharide portions can be, for example, A) enzymatic cleavage reagents such as exoglycosidases and endoglycosidases, B) chemical cleavage reagents such as those used for acetolysis, periodate oxidation for carbon-carbon bond cleavage, and Smith degradation reagents, and C) chemical modification reagents such as methylation reagents, e.g. Me$_2$SO$_4$, used in oligosaccharide structure analysis, and the like.

In an illustrative embodiment of the invention employing enzymatic cleavage reagents the treatment step can comprise: reacting each oligosaccharide sample portion with an array of specific enzyme reagent units which contain various of the plurality of enzymes required to cleave selected disaccharide linkages existing in said oligosaccharide sample, in which each said linkage is cleaved by only one of said enzymes and in which said reagent units are equal in number to the number of oligosaccharide sample portions and composed as follows:

(1) one said reagent unit contains a mixture of all said enzymes, (2) another said reagent unit is a blank which contains none of said enzymes, and (3) the remaining said reagent units each contain a mixture of all said enzymes except one enzyme which is included in each of said other remaining reagent units.

In another illustrative embodiment of the invention an expanded array of enzyme reagent units is used in order to compensate for degeneracy caused by linkages cleaved by more than one of said enzymes.

The following exoenzymes and their specificities illustrate the enzymes which can be used in these enzyme mixes:

TABLE 1

| Enzyme | Specificity (as programmed) |
|---|---|
| Almond alpha-fucosidase I | Fucα1-3/4 |
| Bacillus fulminans alpha-fucosidase | Fucα1-2 |
| Bovine epid. alpha-fucosidase will not cleave Fucα1-3 if there is a 4 branch on the same sugar | Fucα1-3/6 |
| C. lampas alpha-fucosidase | Fucα1-6 |
| Coffee bean alpha-galactosidase | Galα1-3 |
| E. coli beta-galactosidase | Galβ1-4/6 |

TABLE 1-continued

| Enzyme | Specificity (as programmed) |
|---|---|
| Jack bean beta-galactosidase will not cleave Gal β1-4 if there is a 3 branch on sugar to which it is attached | Galβ1-3/4/6 |
| Jack bean beta-hexosaminidase | GalNAc/GlcNAc β1-2/4 |
| S. pneum. beta-hexoaminidase will not cleave if: i. there is a 6 branch on the sugar to which it is attached ii. it is attached to a sugar which is the 6 branch of a sugar with a 4 branch | GlcNAcβ1-2 |
| A. saitoi alpha-mannosidase I | Man α1-2 |
| A. saitoi alpha-mannosidase II will not cleave Man α1-6 if it is on a branched sugar | Man α1-3/6 |
| Jack bean alpha-mannosidase under arm specific conditions Manα1-6 will not be cleaved if there is a 3 branch on the same sugar which is also substituted | Man α1-2/3/6 |
| Achatina fulica (snail) beta-mannosidase | Man β1-4 |
| A. ureaf. sialidase | NeuNAc α2-3/6/8 |
| Almond beta-xylosidase | Xyl β1-2 |

The enzymatic reactions are allowed to proceed for a predetermined period of time or to a desired end point, or allowed to go to completion, to provide a reaction mixture or final cleaved reaction product for each said oligosaccharide portion.

The products from each separate reaction mixture are then combined into a product pool. The prevalence of said products is measured quantitatively and simultaneously to determine the molar proportions of the reaction products. A single analysis may be performed on the pool of all products or, alternatively, one analysis may be performed on, e.g., half the products and another analysis on the other half of the products.

The analysis of the product pool can employ techniques such as the following:

A) size exclusion chromatography such as, for example Bio-Gel ® P-4 gel filtration chromatography [Yamashita et al., *Meth. Enzymol.* 83, 105-126 (1982)], for which product elution volumes can be predicted. Hydrodynamic volumes can be used as shown in Table 2, below.

TABLE 2

Hydrodynamic volume determination
The following rules are used to determine the hydrodynamic volumes of the fragments after enzyme cleavage:

| | |
|---|---|
| Fuc (normal) | 1.0 |
| (exo branching Fuc on the reducing terminus) | 1.0 |
| (exo branching Fuc anywhere else) | 0.5 |
| Gal, Glc, Man, Xyl | 1.0 |
| GalNAc, ManNAc | 2.0 |
| GlcNAc (normal) | 2.0 |
| (exo 4 GlcNAc on a tri-substituted sugar) | 0.5 |
| NeuNAc | 6.0 |
| Reducing terminus | 0.5 |

B) HPLC techniques [Hardy and Townsend, *Proc. Natl. Acad. Sci. USA* 85, 3289-3293 (1988); Twonsend et al., *Nature* 335, 379-380 (1988)], which require an experimental data base to identify the products by comparision to known standards.

C) electrophoresis such as, for example, capillary electrophoresis [Gordon et al., *Science* 242, 224-228

(1988)] and gel electrophoresis which requires an experimental data base to identify the products by comparison to known standards.

Reconstruction or identification of the starting oligosaccharide from the molar prevalence of the reaction products can be carried out by direct interpretation of the analysis results or by comparison of the analysis results with a computergenerated database (based on theoretical or experimental data) or a purely experimental database of results for a large number of oligosaccharides.

Monitoring techniques can be used with the oligosaccharide sequencing method which determine the molar prevalence of each product such as A) amperometric methods, for example, pulsed amperometric detection, B) chemical reactivity methods, for example antibody recognition and mass spectrometry, C) spectroscopic methods, for example, NMR [Vliegenthart et al., Adv. Carb. Chem. & Biochem. 41, 209-374 (1983)], mass spectroscopy, IR, UV and fluorescence, and in the preferred embodiment:

D) radioactivity labeling by reduction of the reducing terminus.

In order to illustrate the invention in greater detail, the RAAM for oligosaccharide sequencing will be described with particular application to the exoglycosidase sequencing of oligosaccharides in the following examples. It will be understood that the invention is not limited to these illustrative examples.

EXAMPLES

Appplication of RAAM to Oligosaccharide Analysis

One of the major prior art techniques for the determination of the covalent structure of biological oligosaccharides is based on sequential exoglycosidase digestion. The oligosaccharide with a radioactively ($^3$H) labeled reducing terminus is treated with a specific exoglycosidase, the reducing terminus product being analyzed on the basis of its hydrodynamic volume using Bio-Gel P-4 chromatography monitored by a radioactivity counter. The product of the first reaction is then treated with a different exoglycosidase and the analysis continued.

In the RAAM method as applied in the present examples to the exoglycosidase sequencing of oligosaccharides, the initial oligosaccharide sample is divided into a number of equal portions. Each portion is treated with a separate mix of exoglycosidases to give a single reducing terminus fragment. The resulting product pool containing all the reducing terminus fragments is analyzed by Bio-Gel P-4 chromatography. The final spectrum is a plot of intensity (counts/minute) versus hydrodynamic volume (glucose units) containing an integral intensity from each reaction mix. As mixtures of exoglycosidases are used for each reaction, the information obtained is different from that of the sequential technique where single enzymes are used (not an inherent property of RAAM but of the enzyme array used).

In the prior art sequential method of oligosaccharide sequencing, the presence of specific linkages is determined by the ability of a given enzyme to cause cleavage. In the RAAM method, the inability of an enzyme mix lacking a given enzyme to cleave that linkage. As all other linkages can be cleaved until that given linkage is reached, that linkage forms a stop point for cleavage by that enzyme mix. The position of the stop point in the oligosaccharide is then determined by the size of the remaining fragment. If that linkage does not occur, no stop point is reached and full cleavage takes place. For instance, one may consider the linear oligosaccharide ABCDE shown in FIG. 1a with linkages cleaved by exoglycosidases a, b, c and d. A mix of exoglycosidases a + c + d will result in a final fragment BCDE (the BC linkage forms the stop point in the absence of exoglycosidase b). However, a sugar lacking the linkage BC will be fully cleaved, thereby resulting in a product E. By using a set of such mixes (an enzyme array) the entire oligosaccharide can be mapped by its pattern of stop points.

Enzyme Array Design

The initial object of the enzyme array is to create a pattern of stop points which will allow the oligosaccharide to be mapped. In order to generate a well defined stop-point pattern, a basic set of enzymes is selected which will fulfill the following requirements:

1. A mix containing all desired enzymes to cleave every possible disaccharide linkage that may occur in the oligosaccharide.

2. There must be no redundancy (i.e., a given linkage must only be cleaved by one enzyme). Enzymes can be monosaccharide and/or linkage specific, but it is preferred that they be not arm specific, otherwise the stop point pattern can change between related compounds. For a linear oligosaccharide, the basic enzyme array is then generated by using:

1. A blank mix with no enzymes — this gives the hydrodynamic volume of the starting product.

2. Mixes, each of which is missing one enzyme — these give the pattern of stop points used to map the structure.

3. A mix containing all enzymes - this should result in a monosaccharide-labeled product (e.g. GlcNAc-labeled for N-linked oligosaccharides) and provides a test to ensure that the oligosaccharide can be fully sequenced by the array being used.

The foregoing set of mixes is called a blanked-diagonal array. Such an array for the linear structure shown in FIG. 1a is given in FIG. 1b and the stop point pattern it generates is shown in FIG. 1a.

For a branched oligosaccharide, such as is shown in FIG. 2a, the same pattern of stop points can be generated by the same procedure, except that a mix of enzymes a + a' is used instead of enzyme a (FIG. 2b).

Once the correct stop point pattern has been generated, extra specificity can be included by expanding the basic array using more selective enzymes. Extra mixes are added, based on the mixes already present and replacing a general enzyme by a more specific enzyme (for instance the array in FIG. 2b can be expanded by adding mixes with the composite enzyme a + a' replaced by the more specific enzyme a, FIG. 2c). Because of the structural limitations, some of these extra mixes may be redundant. The expanded array can then be expanded further for any other more selective reagents by the same process.

FIG. 4 illustrates the effect of using an enzyme array containing four enzymes (A, B, C and D) on a biantennary oligosaccharide. The result of each digestion mix $U_1$ to $U_6$ is tabulated and the final fragment profile can be calculated. The hydrodynamic volumes of each fragment can also be calculated from the glucose units for each oligosaccharide residue (circled numbers). The cleavage point of each enzyme is also shown by broken arrow lines. FIG. 5 shows the computer calculated RAAM Bio-Gel P-4 profiles for the oligosaccharide sequenced in FIG. 4.

A. Test Results on Complex Oligosaccharides

The enzymatic RAAM method is illustrated herein on two oligosaccharides, a complex biantennary (structure I, FIG. 3) and a complex trianntenary (structure II, FIG. 3). The enzyme array used for both these tests is given in FIG. 6, digestions being carried out under arm specific conditions for Jack bean α-mannosidase.

Materials AND Methods

Structures I and II were prepared from the glycoproteins human serum transferrin and bovine fetuin, respectively. Both compounds were radiolabeled at the reducing terminus by reduction with $NaB^3H_4$.

Each sample was divided into seven equal aliquots and digested with the exoglycosidase mixes shown in FIG. 6. These enzyme mixes were prepared in a buffer consisting of 0.1 M citric acid, 0.2 M disodium phosphate and 0.001 % sodium azide, pH 5.0, with enzyme activity as shown in Table 3, below.

TABLE 3

| Enzyme | Activity units/ml |
| --- | --- |
| Jack bean β-galactosidase | 9 |
| Jack bean β-hexosaminidase | 11 |
| Streptococcus pneum. β-hexosaminidase | 0.01 |
| Jack bean α-mannosidase | 1.2 |
| Achitina fulica (snail) β-mannosidase | 0.3 |

One unit of enzyme activity is defined as the amount required to hydrolyze the appropriate 3 mM p-nitrophenyl-glycoside at 37° C. The substrate concentration in each case was 30 μM and the enzyme reactions were carried out at 37° C. for 18 hours under toluene.

The resulting product solutions were pooled for each sample. The intensities of the Bio-Gel P-4 peaks were determined by pooling the fractions corresponding to each peak and measuring the counts per minute in a scintillation counter.

Results

The resulting enzyme RAAM P-4 chromatograms of oligosaccharide structures I and II are shown in FIGS. 7 and 9, respectively, and the position and intensity data summarized in Table 4, below.

TABLE 4

| Oligosaccharide | P-4 position (Glu units) | | P-4 intensity (normalized to 7 units) | |
| --- | --- | --- | --- | --- |
| | Test Results | Computer Calculated | Test Results | Computer Calculated |
| Structure I | 13.6 | 13.5 | 2.0 | 2 |
| | 7.2 | 7.5 | 1.0 | 1 |
| | 5.6 | 5.5 | 1.0 | 1 |
| | 4.4 | 4.5 | 1.0 | 1 |
| | 2.5 | 2.5 | 2.0 | 2 |
| Structure II | 16.4 | 16.5 | 2.0 | 2 |
| | 9.1 | 9.5 | 1.0 | 1 |
| | 7.2 | 7.5 | 1.0 | 1 |
| | 5.5 | 5.5 | 1.0 | 1 |
| | 2.5 | 2.5 | 2.0 | 2 |

From the results it is clear that under these conditions all the exoglycosidases which were used behaved normally, with reactions going to completion to give a single reducing terminus product from each enzyme mix. Normalizing the intensity data to seven (the number of enzyme mixes) gives integer intensity for each peak, as desired. The computer simulated Bio-Gel P-4 RAAM profiles for oligosaccharide structures I and II are shown in FIGS. 8 and 10, respectively, and agree with the experimentally determined Bio-Gel P-4 RAAM profiles.

B. Computer Modeling of Enzyme RAAM Results

A set of FORTRAN 77 programs have been written and implemented on a Micro-Vax II to simulate the foregoing test results of enzyme RAAM applied to oligosaccharides. The computer simulations can then be used to check different test procedures (e.g. to compare results from different enzyme arrays) and to test the theoretical tolerance of the method (e.g. to incomplete enzyme digestion or to the presence of contaminants) without the necessity for extensive experimentation. An accurate computer model also allows databases of calculated results to be generated for libraries of theoretical structures necessary for a general automated analysis method (see below).

Methods

A branched oligosaccharide is represented by a linear character string. The activity of each exoglycosidase is specified in terms of the character strings representing the oligosaccharide subunits on which it will act. The oligosaccharide string is then searched and any regions corresponding to that be repeated on the resulting string for as many enzymes as required. The hydrodynamic volume data from the Bio-Gel P-4 analyses of the final fragment is calculated by summing the contributions of the separate monosaccharide units according to the rules set forth in Table 2, above. This process is then repeated for each separate enzyme mix in the array and the results summed to give the final P-4 profile for the oligosaccharide. The whole procedure has been automated, allowing databases of enzyme RAAM P-4 profiles for any given enzyme array to be generated for as many oligosaccharides as required. The enzyme RAAM P-4 profiles can also be simulated for mixtures of oligosaccharides and for cases of incomplete enzyme digestion.

Results

A comparison between the computer calculated and test enzyme RAAM P-4 profiles of structures I and II using the enzyme array shown in FIG. 6 is given in Table 4, above. As can be seen, the computer programs reproduce the test data very well. The results of enzyme cleavage are accurately reproduced (given the enzyme specificities are known).

These programs have been used to model the results for a large number of oligosaccharides using a variety of enzyme arrays. Typical results for four oligosaccharides are shown in FIG. 11. In this case the enzyme array used includes an α-fucosidase. All four compounds give different RAAM profiles using this array, although they have the same, calculated hydrodynamic volumes and the first three compounds are all closely related. The first (upper) oligosaccharide is structure I.

The effects of both sample impurity and incomplete enzyme digestion on enzyme RAAM P-4 profiles have also been modeled using these programs. FIG. 12 shows calculated RAAM P-4 profiles for a single oligosaccharide (structure I) with a 15% impurity of a related oligosaccharide (upper panel) or with an 85% digestion efficiency for the β-galactosidase (middle panel) or for all enzymes (lower panel) compared to the pure P-4 profile for the same array given in FIG. 11. From these results it is clear that the method is far more sensitive to incomplete enzyme digestion than to sample impurity. In general, a sample purity of 80-85% and enzyme efficiencies of 90-95% would be sufficient to extract the profile of the major component present.

FIG. 13 shows how an expanded blanked diagonal array of enzyme mixes can be used to reduce the degeneracy which may occur by chance. In this illustrative example, the basic blanked diagonal array of the exoglycosidases (enzyme mixes 1 to 6) required to sequence plant oligosaccharides can not discriminate between the two closely related oligosaccharide structures shown. That is, the respective RAAM P-4 profiles for these two oligosaccharides shown in the upper-left and lower-left panels are identical. However, an expanded blanked diagonal array (in which enzyme mixes 6 and 6' are used instead of enzyme mix 6), generates unique RAAM P-4 profiles for the two oligosaccharide structures. Comparison between upper-right and lowerright panels clearly shows the substantial differences in the RAAM P-4 profiles of the respective oligosaccharides.

FIG. 14 shows that the basic blanked diagonal array can be extended to a high level of complexity so as to reduce the possibility of two dissimilar oligosaccharide structures having the same RAAM P-4 profiles. In this illustrative example, a total of seven different exoglycosidases were used to prepare a total of 16 different enzyme mixes to generate the RAAM P-4 profile shown for oligosaccharide structure 1.

Various other examples will be apparent to the person skilled in the art after reading the present disclosure without departing from the spirit and scope of the invention. It is intended that all such other examples be included within the scope of the appended claims.

What is claimed is:

1. A method of sequencing oligosaccharides comprising:
   A. Placing an identifying label on the reducing terminal residue of the oligosaccharide to be sequenced.
   B. Dividing said oligosaccharide into a plurality of separate portions of known integer amounts,
   C. Reacting each said portion with a different reagent mix for a predetermined period of time or to a predetermined end point and in amounts and proportions sufficient to thereby provide a series of reaction mixtures of cleaved reaction products,
   D. Pooling known integer amounts of the products from each separate reaction mixture to give a product pool,
   E. Performing an analysis on said product pool which measures the molar proportions of the reaction products, and
   F. Reconstructing or identifying the starting oligosaccharide from the molar prevalence of said reaction products.

2. The method of claim 1 in which the identifying label is selected from the group consisting of a radioactive label, a spectroscopically active reporter group and a chemically active reporter group.

3. The method of claim 2 in which the identifying label is provided by reduction of the reducing terminal N-acetylglucosamine residues on the oligosaccharide with $NaB^3H_4$.

4. The method of claim 1 in which the reagent mixes are selected from the group consisting of enzymatic cleavage reagents, chemical cleavage reagents and chemical modification reagents.

5. The method of claim 4 in which the reagent mixes comprise exoglycosidases.

6. The method of claim 1 in which the analysis on the product pool is performed by a procedure selected from the group consisting of size exclusion chromatography, HPLC and electrophoresis.

7. The method of claim 6 in which the analysis on the product pool is performed by determining the relative hydrodynamic volumes of the product pool components by acrylamide gel filtration chromatography.

8. The method of claim 1 in which the analysis of pool products is monitored by a procedure comprising detecting the presence of an identifying label on said products selected from the group consisting of a radioactive label, a spectroscopically active reporter group and a chemically active reporter group.

9. A method of sequencing oligosaccharides comprising:
   A. placing an identifying label on the reducing terminus of the oligosaccharide sample to be sequenced,
   B. dividing said oligosaccharide sample into a plurality of equal portions which are two in number more than the number of disaccharide linkages to be determined,
   C. reacting each said oligosaccharide sample portion for a predetermined period of time or to a predetermined end point with an array of specific enzyme reagent units which contain one or more of the plurality of enzymes in amounts and proportions sufficient to cleave selected disaccharide linkages existing in said oligosaccharide sample, in which each said linkage is cleaved by only one of said enzymes and in which said reagent units are equal in number to the number of oligosaccharide sample portions and composed as follows:
      (1) one said reagent unit contains a mixture of all said enzymes,
      (2) another said reagent unit is a blank which contains none of said enzymes, and
      (3) the remaining said reagent units each contain a mixture of all said enzymes except one enzyme which is included in each of said other remaining reagent units,
   D. allowing the enzyme reactions to go to completion to provide a final cleaved product for each said oligosaccharide sample portion, and
   E. pooling said cleaved products and determining the identity of the oligosaccharide sample by measuring the prevalence of said products quantitatively and simultaneously.

10. A method of sequencing oligosaccharides comprising:
   A. placing an identifying label on the reducing terminus of the oligosaccharide sample to be sequenced,
   B. dividing said oligosaccharide sample into a plurality of equal portions which are more in number than the number of disaccharide linkages to be determined,
   C. reacting each said oligosaccharide sample portion for a predetermined period of time or to a predetermined end point with an array of specific enzyme reagent units which contain one or more of the plurality of enzymes in amounts and proportions sufficient to cleave selected disaccharide linkages existing in said oligosaccharide sample, in which each said linkage is cleaved by at least one of said enzymes, in which one or more of said linkages is cleaved by more than one of said enzymes and in which the number of said reagent units is sufficient to compensate for degeneracy caused by linkages cleaved by more than one of said enzymes and composed as follows:
(1) one said reagent unit is a blank which contains none of said enzymes, and
(2) the remaining said reagent units each contain a different mixture of said enzymes,
D. allowing the enzyme reactions to go to completion to provide a final cleaved product for each said oligosaccharide sample portion, and
E. pooling said cleaved products and determining the identity of the oligosaccharide sample by measuring the prevalence of said products quantitatively and simultaneously.

* * * * *

UNITED STATES PATENT AND TRADEMARK OFFICE
CERTIFICATE OF CORRECTION

PATENT NO. : 5,100,778

DATED : March 31, 1992

INVENTOR(S) : Thomas W. Rademacher et al.

It is certified that error appears in the above-identified patent and that said Letters Patent is hereby corrected as shown below:

At col. 7, line 63, the following clause was omitted and should be inserted after the word "method,": --the presence of a given linkage is determined by--. At col. 10, line 31, the following clause was omitted and should be inserted after the word "that": --for a given enzyme activity are deleted. The process can--.

Signed and Sealed this

Tenth Day of August, 1993

Attest:

MICHAEL K. KIRK

Attesting Officer

Acting Commissioner of Patents and Trademarks